United States Patent [19]

Stern et al.

[11] Patent Number: 5,434,282

[45] Date of Patent: Jul. 18, 1995

[54] DOUBLE-BRANCHED COMPOUNDS AND PROCESSES FOR THEIR PRODUCTION

[75] Inventors: Robert Stern, Paris; Gérard Hillion, Herblay; Abakar Kotoko, Paris; Yves Chauvin, Le Pecq, all of France

[73] Assignee: Institut Francais du Petrole, Rueil Malmaison, France

[21] Appl. No.: 231,706

[22] Filed: Apr. 22, 1994

[30] Foreign Application Priority Data

Apr. 23, 1993 [FR] France ................... 93 04923

[51] Int. Cl.⁶ .............. C07C 69/24; C07C 67/03; C07C 53/126; C07C 51/36
[52] U.S. Cl. .................. 554/223; 554/227; 562/546
[58] Field of Search ........... 554/223, 227; 562/546

[56] References Cited

U.S. PATENT DOCUMENTS

| | | | |
|---|---|---|---|
| 3,162,658 | 12/1964 | Baltes et al. | 260/405.6 |
| 3,865,853 | 2/1975 | Hinze | 260/409 |
| 3,966,798 | 6/1976 | Intille et al. | 260/486 R |
| 4,318,860 | 3/1982 | Hsu et al. | 260/405.5 |

FOREIGN PATENT DOCUMENTS

| | | |
|---|---|---|
| 2202727 | 5/1974 | France . |
| WO91/11426 | 8/1991 | WIPO . |
| WO91/11428 | 8/1991 | WIPO . |

OTHER PUBLICATIONS

Blum et al., "Catalytic Hydrogenation of Olefins, Acetylenes and Arenes by Rhodium Trichlorid and Aliquat-336 Under Phase Transfer Conditions," *Tetrahedron Letters*, vol. 24, No. 38, pp. 4139–4142, Jul. 1983.

Dejarlais et al., "Conjugation of Polyunsaturated Fats: Activity of Some Group VIII Metal Compounds," *Journal of the American Oil Chemists' Society*, vol. 48, pp. 157–159, Jun. 1970.

Conjugation of Polyunsaturated Fats: "Methyl Linoleate With Tris(triphenylphosphine) Chlorodium," *Journal of the American Oil Chemists' Society*, pp. 21–24, Jan. 1971.

*Primary Examiner*—Arthur C. Prescott
*Attorney, Agent, or Firm*—Millen, White, Zelano & Branigan

[57] ABSTRACT

A novel family of chemical compounds derived from fatty compounds has two branches of two carbon atoms on the linear chain and general formula $C_{21}H_{39}COOR$ where R represents a hydrogen atom, a lower alkyl radical or a glyceryl radical. Particular compounds for consideration have the following formulae:

$$(C_2H_5)_2C_{17}H_{29}COOR \qquad (I)$$

$$(C_2H_5)(C_2H_4)C_{17}H_{30}COOR \qquad (II)$$

and $$(C_2H_5)(C_2H_3)C_{17}H_{31}COOR \qquad (III)$$

also compounds with the following formulae derived from partial or total hydrogenation of the above:

$$(C_2H_5)_2C_{17}H_{31}COOR \qquad (IV)$$

$$(C_2h_5)(C_2h_4)C_{17}H_{32}COOR \qquad (V)$$

and ti $(C_2H_5)_2C_{17}H_{33}COOR \qquad (VI)$

Compounds with formulae (I), (II) and (III) may be produced by addition of ethylene to compositions comprising mainly diunsaturated $C_{18}$ fatty acids; or to lower alkyl or glyceryl esters of these acids, originating in particular from natural oils, in the presence of a catalytic system containing anionic rhodium of the type $[RhX_4]^- YR'_4$ where X is preferably a halide anion; Y is a nitrogen $N^+$ or phosphorous $P^+$ atom and $R'$ is preferably a hydrocarbon group.

Compositions in accordance with the invention can be used as base compositions for lubricants or emulsifying agents.

22 Claims, 2 Drawing Sheets

DOUBLE-BRANCHED COMPOUNDS AND PROCESSES FOR THEIR PRODUCTION

BACKGROUND OF THE INVENTION

The invention concerns a novel family of chemical compounds derived from fatty compounds, characterised by the presence of two branches on the linear chain. These compounds are obtained by addition of ethylene to polyunsaturated compounds. The invention also concerns a process for the production of these compounds using anionic rhodium complexes in the presence of ethylene and certain fatty compounds.

The invention still further concerns the production of saturated derivatives of these double-branched compounds by partial or total hydrogenation of the primary compounds.

It has been known for more than 30 years that ethylene can be reacted with different dienes (U.S. Pat. No. 3,502,738). 1,4-hexadiene is obtained from butadiene, 3-methylhexadiene is obtained from isoprene and 2-vinylpentene is obtained from piperylene, each in the presence of various rhodium complexes. Ethylene has also been reacted with dienes whose two double bonds are within the body of the chain, one or both extremities being substituted by alkoxy or halogen groups (U.S. Pat. No. 3,742,080).

Ethylene or propylene is also known to react with fatty dienes, either of the vinyl-octadecenoate type when adding an ethylene group, which may or may not be conjugated, to produce single-branched compounds, or of the isobutyl-octadecenoate type if two ethylene groups are added, or of the isohexenyl-octadecenoate type if three ethylene groups are added to the fatty compound; the fatty compound usually used is a conjugated linoleic ester.

Addition of ethylene to produce single-branched derivatives is described in international patent application WO-91/11428 A1 and single-branched hydrogenated compounds are described in international patent application WO-91/11426 A1.

Ethylene derivatives were also obtained more than twenty years ago by D. G. Chasin et al using a Wittig reaction en the ketone in position 10. Hydrogenation of the ethylenated compound obtained enabled the author to make the corresponding alkyl 10-ethyl stearate (Chem Phys Lipids 6 8-30 (1971)).

Dimethyl stearate type compounds produced by skeletal isomerisation are also known but many other isomers are produced at the same time.

None of the prior art describes fatty derivatives having two branches each comprising two carbon atoms.

SUMMARY OF THE INVENTION

The invention provides precisely this type of compound, in which the attachment points of the two branches are different and the branches are located towards the centre of the chain.

The advantage of these double-branched compounds lies in their very low pour point, far lower than that of derivatives with only one branch.

The particular advantage of ethyl groups over methyl groups resides in the greater biodegradability of the former.

The compounds of the invention, which may be considered as particular isostearic acids, are those of known isostearic acids, particularly in the manufacture of metallic salts, emulsifying agents, plasticizers and lubricants.

The invention includes compounds in their acid form and as lower alkyl or glyceryl esters, also compounds derived therefrom, such as heavier alkyl esters, formed with a number of alcohols, amides formed with amines, and amine salts, metallic salts and alkylolamides.

The novel family of chemical compounds of the invention may be defined by the following formulae:

  (I)

  (II)

  (III)

  (IV)

  (V)

  (VI)

the positioning of the $C_2H_5$, $C_2H_4$ and/or $C_2H_3$ groups on the chain is schematically represented by the following structures a, b and c.

In formulae (I) to (VI), the different pairs of groups a, b, c (i.e., aa, ab, ba, ac and ca) may be in positions 9-11, 9-12, 10-12, or 10-13.

R may be an alkyl or alkenyl radical or a hydrogen atom.

In general, R=H, $CH_3$, $C_2H_5$, $C_nH_{2n+1}$, or glyceryl.

Compounds having formulae (IV), (V) and (VI) are respectively obtained by partial or total hydrogenation of compounds with formulae (I), (II) and (III).

Fatty compounds which may be employed in the reaction with ethylene in accordance with the invention are, for example, polyunsaturated oils such as sunflower seed oil, safflower soya, rape seed oil, preferably oils which are rich in dienes or trienes, also derivatives of these oils such as diunsaturated fatty acids and methyl esters thereof. Conjugated diunsaturated compounds are preferably used. Conjugation is achieved using either rhodium complexes or with potassium alcoholates which, according to a known processes, produces 9-11 ct and 10-12 tc isomers.

The catalyst employed is rhodium based, but only one particular family of complexes can produce this addition of two ethylene groups at different locations along the chain.

This specific family of rhodium catalysts is characterised by the following formula:

$$[RhX_4][YR'_4]^+ \quad (VII)$$

where $X = Cl$, $Br$, $F$, $SO_3^-$, $R'$, $OH^-$, $OR'^-$, $R'^-$ or $SO_4^{--}$; $y = N^+$ or $P^+$; and $R' = $ alkyl, cycloalkyl, aryl, alkylaryl, alkenyl or acyl. A polymeric group such as polystyrene may also be included among the alkyl groups.

In formula (VII), X may also be different but at least one of them must be a halide.

R' groups may be different to each other.

The following quaternary salts may in particular be cited:

$N(CH_3)_4Br$, $N(C_2H_5)_4Br$, $N(C_3H_5)_4Br$, $N(C_6H_{13})_4Br$, $N(C_{12}H_{25})_4Br$, $N(C_{18}H_{35})_4Br$ or their corresponding chlorides, and preferably also mixed compounds such as hexadecyl trimethyl ammonium chloride, octadecyl trimethyl ammonium chloride, didecyl dimethyl ammonium chloride, lauryl pyridinium chloride, dimethyl dibenzyl ammonium chloride and dimethylstearyl benzyl ammonium chloride.

The majority of the quaternary salts defined above are cheap and readily available since they constitute starting materials for detergents, softeners or bactericides.

The counter-ion is, more particularly, a sulphate, sulphonate or, preferably for the reaction, a halide.

The most complex case is where the quaternary salts include a polymeric group (as, for example, those sold by FLUCKA) based on ammonium or phosphonium with a polystyrene group.

Finally, a non ionic phosphorane derivative $P\theta_3 = CH - CO - \theta$ exists which reacts to form an ionic complex with $RhCl_3$ of type

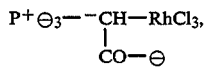

$\theta$ representing a phenyl radical. The reaction conditions are fairly flexible. The pressure of the ethylene can vary between, for example, 0.1 and 30 MPa, preferably 0.3 to 4 MPa, and the temperature, for example, from 20° C. to 160° C., preferably 90° C. to 120° C. The duration can vary between 1 hour and 24 hours. The rhodium complex concentration, when operating with a homogeneous catalyst, is for example in a molar ratio with the fatty substrate of the order of 1/50 to 1/5000.

The ethylene addition reaction may be carried out in a batch process and the catalyst can be recovered at the end of the reaction using activated earth or a basic resin based polymer.

Following elimination of the catalyst, the double-branched compounds can be hydrogenated, using nickel, palladium or platinum catalysts, for example, or even using the same catalyst.

If the catalyst is supported on a polymer, it can be filtered and reused several times in succession.

The catalyst is initially formed by addition of 1 to 4 moles of quaternary salts to one of rhodium III compound, generally a rhodium chloride or bromide. This reaction is normally carried out in a solvent which can subsequently be evaporated off. The reaction can be formulated as follows:

$$RhX_3 + {^+YR'_4X} \rightarrow [RhX_4]^- {^+YR'_4}$$

These rhodium compounds are amply described, for example by Blum for the hydrogenation of various compounds (cf Blum, Tetrahedron Letters 24, 4139-4142 (1983)).

The reaction may also be carried out in two phases in the presence of a hydrophilic solvent.

It can be shown that the rate of ethylene addition is accelerated with reference to a reaction with rhodium chloride or phosphine or phosphite compounds.

The decomposed portion of the rhodium complex produces traces of the isobutenyl compound.

With reference to a reaction with non ionic complexes, reaction rates of 100 times greater can be obtained.

Figure 1:
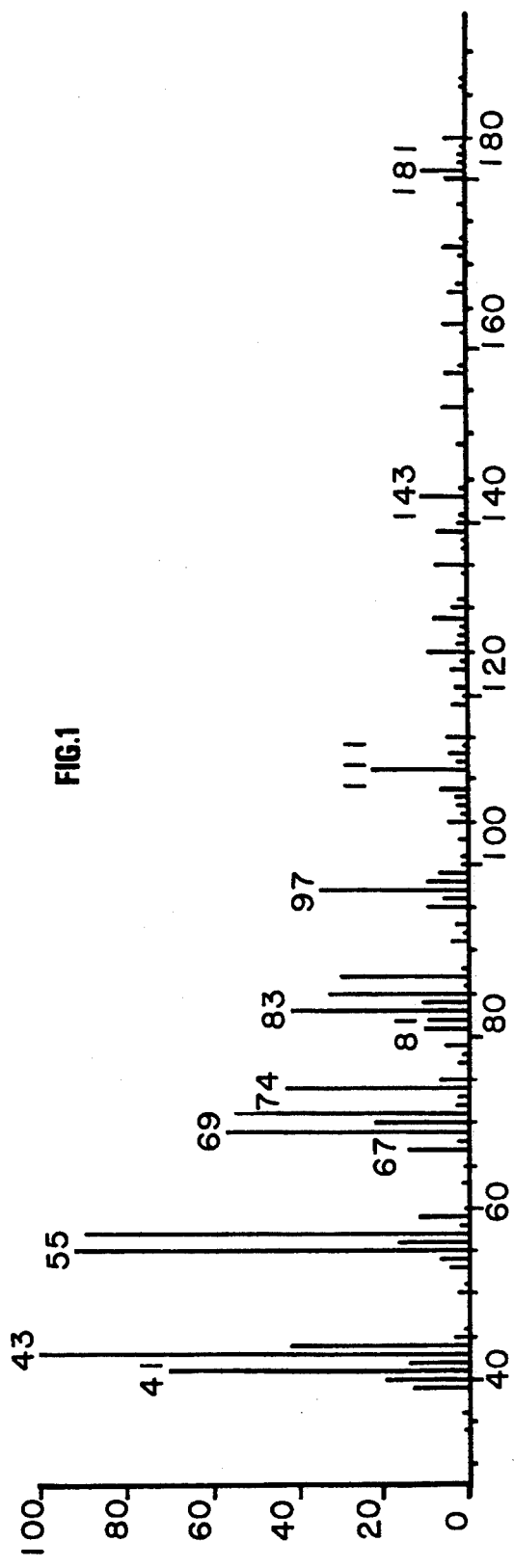
FIGS. 1 and 1A represent the mass spectrography spectrum of methyl 9,12-diethylstearate.

Each pair of FIGS. (1 and 1A; 2 and 2A) constitute one continuous spectrum with masses from 0 to 360 along the abscissae axis. The heights of the lines corresponding to the main fragments of the molecule are expressed with an arbitrary unit, along the ordinate axis.

The following examples illustrate the invention.

EXAMPLES

Example 1

0.22 g (0.74 mmol) of $PBu_4Cl$ (tetrabutyl phosphonium chloride) was introduced into a 100 ml flask containing 20 m of chloroform in an argon atmosphere. After the salt had dissolved, 0,2 g of $RhCl_3$, $3H_2O$ (trihydrated rhodium trihydrate) and 1 ml of methanol was added. This was stirred for 30 min at room temperature. A reddish transparent solution of $RhCl_4^{--+}PBu_4$ was obtained. This solution was injected into an autoclave (0.5 l) containing 100 ml (299 mmol) of the methyl ester of sunflower seed oil containing 61 % of cis/trans conjugated compounds by the action of potassium terbutylate on the methyl ester of sunflower seed oil at 130° C. This was heated to 50° C. Ethylene was introduced at 5 bars and heating was continued to 80° C. with slow stirring. Once this temperature had been reached, the ethylene pressure was increased to 30 bars and stirring was continued at 1500 rpm.

The progress of the reaction was followed by removing samples for gas chromatographical analysis (Table 1) and measurement of ethylene absorption. Hydrogenation produced a simpler chromatogram.

TABLE 1

RESULTS OF EXAMPLE 1 WITH A SLIGHT 2:1 PRODUCT PREFERENCE
(2 ethylene/conjugated ester)

| Smpl No | T min | $C_{18:2}ct$ wt % | $C_{18:2}tt$ wt % | A wt % | B wt % | C wt % | D wt % | E wt % |
|---|---|---|---|---|---|---|---|---|
| 1 | 57 | 9 | 15 | 60.4 | 0 | 15 | 0 | 0 |
| 2 | 131 | 1 | 7 | 47.7 | 3.2 | 25.5 | 14 | 1.4 |
| 3 | 228 | 1 | 5 | 32 | 4.5 | 27.5 | 27 | 3 |
| 4 | 307 | 0 | 3.8 | 21.9 | 5.2 | 27.8 | 36 | 5.3 |

The results shown relate to an initially 100% conjugated linoleic acid ester.

A: non conjugated vinyl isomers of 1:1 product (1 branch),
B: isomers of 1:1 product (1 branch),
C: conjugated isomers of 1:1 product (1 branch),
D: 2:1 product isomers with two branches,
E: 2:1 product isomers with isobutyl branching,
ct: cis-trans; tt: trans-trans.

It can be seen that 36% of the 2:1 product with two ethylene branches (sample 4; product D) was obtained at 96% conversion.

Figure 1A:
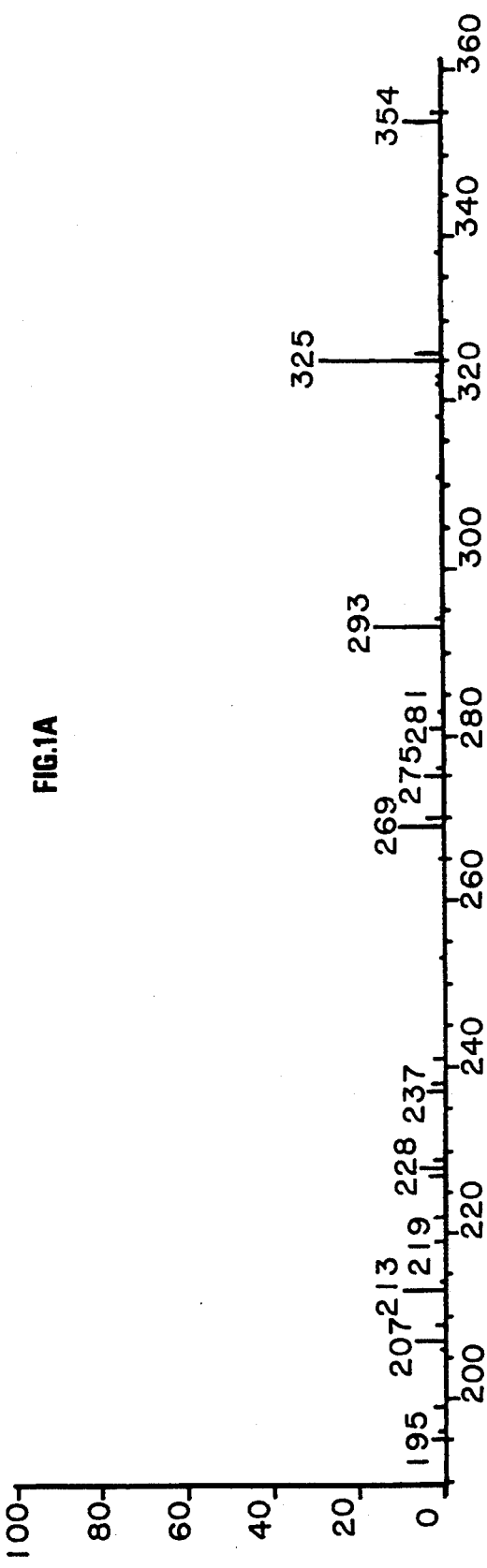

The molecular weight, measured by mass spectroscopy, was 354 after hydrogenation. Analysis of these derivatives was carried out using gas chromatography coupled to a spectroscope. Compounds with MWt=354 were, according to mass spectroscopy, diethylstearates which could be seen in the isomer spectra by analysis of the fragments. FIGS. 1 and 1A show a sample spectrum for one of the compounds. It can be seen from the two schematic structures A and B below that the diethylstearates behave very differently on fragmentation to single branched compounds.

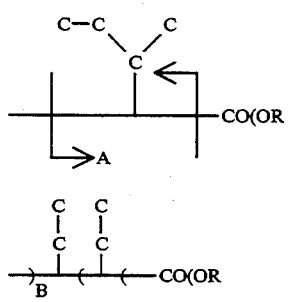

Fragmentation of a single branched compound as indicated in D. G. CHASSIN, Chem Phys Lipids 6 8-30 (1971) should occur in accordance with scheme A above. The mass spectogram was, however, very different and that of product B, where more fragments could be detected.

More detailed examples are given below for a diethyl and an isobutyl derivative, namely methyl 9,12-diethyl stearate and 10-isobutyl stearate (see Tables 2 and 3).

TABLE 2

Fragments obtained by mass spectrography of methyl 9,12-diethyl stearate.

| | |
|---|---|
| M = | 354 |
| M − A = | 325 |
| B − A = | 293 |
| M − C = | 269 |
| B − C = | 237 |
| M − E = | 227 |
| M − K = | 213 |
| B − (A + C) = | 207 |
| B − E = | 195 |
| J = | 197 |
| M − G = | 199 |
| B − K = | 181 |
| B − G = | 167 |
| M − I = | 157 |

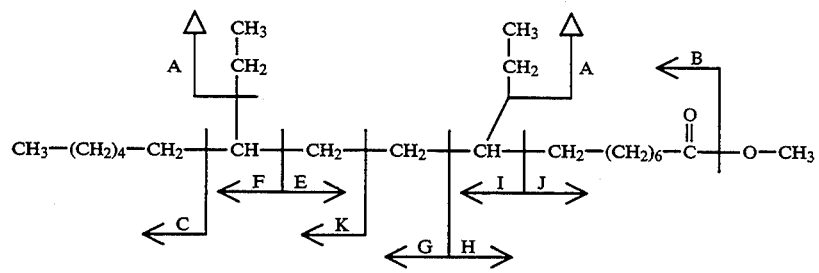

The corresponding spectrum is shown in FIGS. 1 and 1A.

TABLE 3

Fragments obtained from mass spectrography of a methyl 10-isobutyl stearate.

| | |
|---|---|
| M = | 354 |
| M − A = | 297 |
| B − A = | 265 |
| M − C = | 241 |
| M − E = | 171 |
| B − C = | 209 |
| M − T = | 281 |

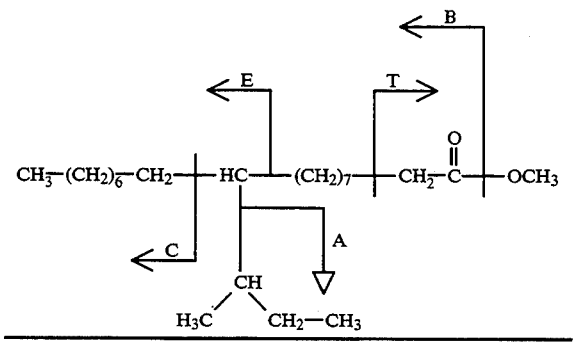

Table 3 shows that the fragments correspond to practically all possible fractions. The same fragments were found in the real spectrum (see the corresponding spectrum shown in FIGS. 2 and 2A).

Figure 2:
FIGS. 2 and 2A represent the mass spectrography spectrum of methyl 10-isobutylstearate.
Figure 2A:
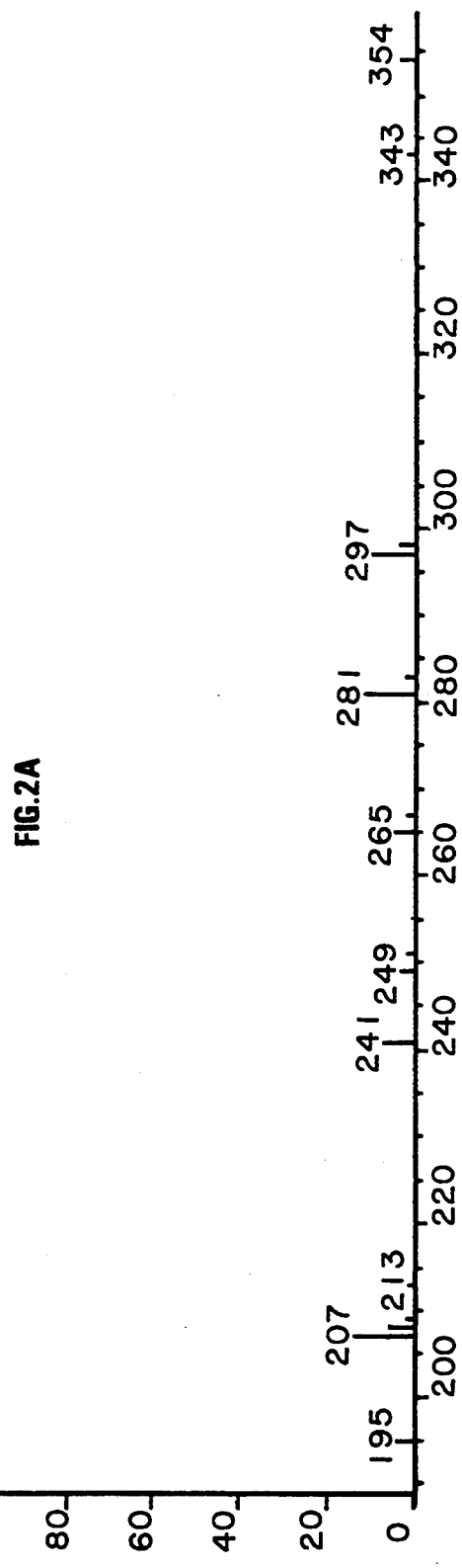

The other peaks corresponding to isomers with molecular weight 354 show that the fragmentations correspond to diethyl groups in the 10-13, 10-12, 9-12 and 9-11 positions (FIGS. 1 and 1A). With an isobutyl, it can be shown that a large fragment at 57 separates, as shown in the table and mass spectrum of the isobutyl derivative (FIGS. 2 and 2A). Not all the fractions observed for the diethyl stearate were observed in this case.

The methyl diethyl stearate derivative had particularly interesting properties. The melting point of the mixture was −55° C., ie, particularly low. The melting point of the acid form was below −18° C.

All the diethyl compounds were characterised by initial loss of a large ethyl fragment, which was not observed in the case of the isobutyl compound.

Example 2

Example 1 was repeated except that the ethylene pressure was 2 MPa.

TABLE 2

| No | T h | $C_{18:2}$ct wt % | $C_{18:2}$tt wt % | A wt % | B wt % | C wt % | D wt % | E wt % |
|---|---|---|---|---|---|---|---|---|
| 1 | 2.25 | 3 | 6 | 56.8 | 2 | 21 | 11 | 0 |
| 2 | 4 | 0 | 2.8 | 34 | 4.5 | 28 | 29 | 1.7 | ct = cis-trans
tt = trans-trans

Products A, B, C, D, E correspond to the products defined in Example 1.

It can be seen here that less than 2 % of the isobutyl compound was formed (sample 2; product E).

Example 3

In this example, the catalyst was synthesised from 1.48 mmol of trihydrated rhodium trichloride and 1.48 mmol of tetrabutyl phosphonium chloride.

300 mmol of cis/trans conjugated $C_{18:2}$ was used. The reaction conditions were 90° C. and 2 MPa of ethylene. Conjugated ester only was measured.

TABLE 3

| No | T h | $C_{18:2}$ct wt % | $C_{18:2}$tt wt % | A wt % | B wt % | C wt % | D wt % | E wt % |
|---|---|---|---|---|---|---|---|---|
| 1 | 3 | 0 | 0.5 | 33.7 | 6.5 | 24.7 | 32 | 2.6 |
| 2 | 5 | 0 | 0 | 29 | 6.5 | 25 | 35 | 3.5 |

Example 4

Example 3 was repeated, this time using 91 mmol of conjugated $C_{18:2}$ and 1.48 mmol of $[RhCl_4]^-[PBu_4]^+$, analysing the samples sooner.

TABLE 4

| No | T min | $C_{18:2}$ct wt % | $C_{18:2}$tt wt % | A wt % | B wt % | C wt % | D wt % | E wt % |
|---|---|---|---|---|---|---|---|---|
| 1 | 49 | 8.4 | 16 | 60 | 1 | 9 | 3.9 | 0 |
| 2 | 104 | 0 | 0 | 30 | 4.8 | 32 | 29.4 | 2 |
| 3 | 184 | 0 | 0 | 13 | 6 | 30 | 46 | 3 |
| 4 | 284 | 0 | 0 | 8 | 5 | 30 | 52 | 3 |

It can be seen that after 50 minutes there was already 60% of the single branched derivative and no trace of isobutenyl. The single-branched derivative was converted into the double-branched derivative.

Example 5

In this example, 100 g of the product of an ethylene addition reaction following the conditions of example 1 was used. The composition is shown in sample No 0 in the following table.

The initial product contained 184 mmol of conjugated compounds ($C_{18:2}$ ct tt). The catalytic solution was constituted by 1.85 mmol of $RhCl_3$, $3H_2O$ and 1.85 mmol of $PBu_4Cl$.

The reaction conditions were the same as those given for Example 1.

TABLE 5

| No | T min | $C_{18:2}$ct wt % | $C_{18:2}$tt wt % | A wt % | B wt % | C wt % | D wt % | E wt % |
|---|---|---|---|---|---|---|---|---|
| 0 | 0 | 15 | 5.4 | 42.6 | 1.7 | 29 | 5.5 | 0 |
| 1 | 150 | 0 | 0 | 6 | 4.7 | 30 | 56 | 2 |
| 2 | 230 | 0 | 0 | 3 | 3.5 | 24.7 | 65 | 3 |
| 3 | 280 | 0 | 0 | 0 | 2.7 | 19 | 74 | 4 |

It can be seen here that the conversion rate to the double-branched derivative was 74%.

Example 6

A product obtained as described in Example 5 was hydrogenated on charcoal at 100° C. by the complex $[RhCl_4]^-[PBu_4]^+$. The initial product contained methyl oleate ($C_{18}$ monounsaturated ester). After hydrogenation, the stearate formed from oleate and the palmitate already present in the initial substrate produced a mixture with a cloud point of −10° C.

Elimination of the straight-chain saturated esters by crystallization from acetone produced a mixture with a cloud point as low as −55° C.

Hydrolysis of the purified dibranched (and some monobranched) esters produced an acid form which essentially consisted of a mixture of monoethyl and diethyl stearic acids, also with a fairly low cloud point (−18° C.).

The composition of the methyl ester mixture obtained after esterification of the crystallized acid mixture was as follows:

1:1 product = 25 % by weight
2:1 diethyl product = 75 % by weight
2;1 isobutyl product = traces

Example 7

In this example, sunflower seed oil was used in a system identical to that described in Example 1.

TABLE 7

| No | T min | $C_{18:2}$ wt % | $C_{18:2}$ct wt % | $C_{18:2}$tt wt % | Prd 1:1 wt % | Prd 2:1 wt % |
|---|---|---|---|---|---|---|
| 1 | 148 | 73.3 | 2.6 | 3.2 | 16.3 | 4.6 |
| 2* | 293 | 47.4 | 0 | 0 | 15.6 | 37 |

*Injection of new catalytic solution (0.37 mmol).

The results recorded are for 69% by weight of $C_{18:2}$ contained in the sunflower seed oil.

It should be noted that the selectivity of the addition product with two moles of ethylene for one of ester is relatively high with respect to reactions with the ester. The reaction was, however, much slower, although it was more rapid than with rhodium chloride.

Example 8

In this example, 1.48 mmol of trihydrated rhodium trichloride and 1.48 mmol of dimethyl benzyl stearyl ammonium chloride in 20 ml of chloroform was used. 50 ml of sunflower seed oil was reacted in 60 ml of heptane in the presence of the catalyst at a pressure of 2 MPa of ethylene at 90° C. After 7 hours of reaction, the reaction product was hydrogenated to obtain: 19 % by weight of 1:1 product and 51% by weight of 2:1 product.

In general, the double-branched organic compounds of the invention can be used for the same applications as their mono-branched or unbranched precursors.

The entire disclosures of all applications, patents, and publications cited herein and of corresponding French Application 93/04923, filed Apr. 23, 1993, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A double-branched organic diene comprising a linear hydrocarbon chain having 18 carbon atoms, wherein said linear hydrocarbon chain carries two lateral chains, each with 2 carbon atoms, and wherein it has one of the following general formulae:

$$(C_2H_5)_2C_{17}H_{29}COOR \quad (I)$$

$$(C_2H_5)_2(C_2H_4)C_{17}H_{30}COOR \quad (II)$$

and $$(C_2H_5)_2(C_2H_3)C_{17}H_{31}COOR \quad (III)$$

where R represents a hydrogen atom, a lower alkyl radical, a lower alkenyl radical or a glyceryl radical.

2. A double-branched organic compound wherein said compound has one of the following general formulae:

$$(C_2H_5)_2C_{17}H_{31}COOR \quad (IV)$$

$$(C_2H_5)_2(C_2H_4)C_{17}H_{32}COOR \quad (V)$$

wherein R is a hydrogen atom, a lower alkyl radical, a lower alkenyl radical or a glyceryl radical.

3. A double-branched organic compound of the following general formula:

$$(C_2H_5)_2C_{17}H_{33}COOR \quad (VI)$$

wherein R is a hydrogen atom, a lower alkyl radical, a lower alkenyl radical or a glyceryl radical.

4. A process for the production of a compound according to claim 1, comprising reacting ethylene with at least one carboxylic acid having a linoleic chain which may optionally be conjugated, or with at least one lower alkyl, lower alkenyl or glyceryl ester of at least one such acid, in proportions of about 2 moles of ethylene per linoleic chain of said acid or ester, in the presence of an anionic rhodium catalyst.

5. A process according to claim 4, wherein said reaction is carried out at a temperature of 20° C. to 160° C. and pressure of 0.1 to 30 MPa.

6. A process according to claim 4 wherein the anionic rhodium catalyst is represented by the formula $$[RhX_4]^-[YR'_4]^+$$

where X represents a halogen atom or a OH$^-$, OR'$^-$, R'$^-$, SO$_3$–R' or SO$_4$– – group, Y represents a nitrogen atom or a phosphorous atom, and R' represents an alkyl, cycloalkyl aryl, alkylaryl alkenyl or acyl polymer radical.

7. A process according to claim 4, wherein said anionic rhodium catalyst is a compound of the formula:

$$[RhCl_4]^{-+}NBu_4 \text{ and } [RhCl_4]^{-+}N(Me_2)(St)Bzl$$

where Bu represents a butyl radical, Me is a methyl radical, St an octadecyl radical, and Bzl a benzyl radical.

8. A process according to claim 4, wherein, in said anionic rhodium catalyst, the rhodium is supported on an anionic complex containing a polystyrene ligand.

9. A process according to claim 4, wherein said anionic rhodium catalyst is a compound of the formula:

$$[RhCl_4]^{-+}PBu_4.$$

10. A process for the production of a partially hydrogenated compound, comprising partially hydrogenating at least one compound according to claim 1, in the presence of a hydrogenation catalyst.

11. A process for the production of a completely hydrogenated compound, comprising completely hydrogenating at least one compound according to claim 1, in the presence of a hydrogenation catalyst.

12. A process according to claim 11, wherein the product obtained substantially in the form of the diethyl stearic acid or low alkyl diethyl stearate is crystallized at low temperature from a solvent to separate any stearic, monoethylstearic and palmitic compounds which may be present.

13. In a method of lubricating a surface with a lubricating agent, the improvement which comprises employing a lubricating agent comprising a compound according to claim 1.

14. In a method of forming an emulsion with an emulsifying agent, the improvement which comprises employing an emulsifying agent comprising a compound according to claim 1.

15. In a method of lubricating a surface with a lubricating agent, the improvement which comprises employing a lubricating agent comprising a compound according to claim 2.

16. In a method of lubricating a surface with a lubricating agent, the improvement which comprises employing a lubricating agent comprising a compound according to claim 3.

17. In a method of forming an emulsion with an emulsifying agent, the improvement which comprises employing an emulsifying agent comprising a compound according to claim 2.

18. In a method of forming an emulsion with an emulsifying agent, the improvement which comprises employing an emulsifying agent comprising a compound according to claim 3.

19. A double-branched organic compound according to claim 1, of formula (I):

$$(C_2H_5)_2C_{17}H_{29}COOR \quad (I).$$

20. A double-branched organic compound according to claim 1, of formula (II):

$$(C_2H_5)_2(C_2H_4)C_{17}H_{30}COOR \quad (II).$$

21. A double-branched organic compound according to claim 1, of formula (III):

$$(C_2H_5)_2(C_2H_3)C_{17}H_{31}COOR \quad (III).$$

22. A double-branched organic compound according to claim 1, wherein R is H, CH$_3$ or C$_2$H$_5$.

* * * * *